United States Patent
Sells et al.

(10) Patent No.: US 11,007,525 B2
(45) Date of Patent: May 18, 2021

(54) VENTED MICROFLUIDIC RESERVOIRS

(71) Applicant: Hewlett-Packard Development Company, L.P., Houston, TX (US)

(72) Inventors: Jeremy Sells, Corvallis, OR (US); Chantelle E. Domingue, Corvallis, OR (US); Robert Moline, Corvallis, OR (US); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 225 days.

(21) Appl. No.: 15/547,756

(22) PCT Filed: Jan. 30, 2015

(86) PCT No.: PCT/US2015/013677
§ 371 (c)(1),
(2) Date: Jul. 31, 2017

(87) PCT Pub. No.: WO2016/122560
PCT Pub. Date: Aug. 4, 2016

(65) Prior Publication Data
US 2018/0021778 A1    Jan. 25, 2018

(51) Int. Cl.
*B01L 3/00* (2006.01)
*G01N 33/487* (2006.01)
*C12M 3/06* (2006.01)
*C12M 1/00* (2006.01)
*C12M 1/36* (2006.01)

(52) U.S. Cl.
CPC ....... *B01L 3/502723* (2013.01); *C12M 23/16* (2013.01); *C12M 29/20* (2013.01); *C12M 41/48* (2013.01); *G01N 33/48707* (2013.01); *B01L 2200/0684* (2013.01); *B01L 2200/10* (2013.01); *B01L 2300/0681* (2013.01); *B01L 2300/0816* (2013.01); *B01L 2400/0439* (2013.01); *B01L 2400/0442* (2013.01)

(58) Field of Classification Search
None
See application file for complete search history.

(56) References Cited

U.S. PATENT DOCUMENTS

| | | | |
|---|---|---|---|
| 5,143,084 | A | 9/1992 | Macemon et al. |
| 5,338,435 | A | 8/1994 | Betts et al. |

(Continued)

FOREIGN PATENT DOCUMENTS

| | | |
|---|---|---|
| CN | 101907629 | 12/2010 |
| CN | 102150042 | 8/2011 |

(Continued)

OTHER PUBLICATIONS

Diao, et al; "A Three-Channel Microfluidic Device for Generating Static Linear Gradients and its Application to the Quantitative Analysis of Bacterial Chemotaxis"; Dec. 13, 2005.

(Continued)

*Primary Examiner* — Matthew D Krcha
(74) *Attorney, Agent, or Firm* — Fabian VanCott

(57) ABSTRACT

Vented microfluidic reservoirs can include a housing and a vent coupled to the housing to vent air associated with a fluid sample communicated into the housing to an environment surrounding a microfluidic device coupled to the housing.

20 Claims, 4 Drawing Sheets

(56) References Cited

U.S. PATENT DOCUMENTS

| | | | |
|---|---|---|---|
| 6,168,948 B1* | 1/2001 | Anderson | B01F 11/0266 366/DIG. 3 |
| 8,329,437 B1 | 12/2012 | Ayliffe | |
| 2002/0168298 A1 | 11/2002 | Huhn et al. | |
| 2003/0035758 A1* | 2/2003 | Buechler | B01D 61/18 422/534 |
| 2004/0147032 A1 | 7/2004 | Martin et al. | |
| 2005/0180891 A1* | 8/2005 | Webster | B01L 3/50273 422/505 |
| 2005/0266582 A1* | 12/2005 | Modlin | B01L 3/5027 436/164 |
| 2006/0280653 A1 | 12/2006 | Harding | |
| 2010/0120083 A1* | 5/2010 | Ritzen | B01L 3/502723 435/30 |
| 2011/0027873 A1* | 2/2011 | Cho | B81B 3/0094 435/287.1 |
| 2011/0171754 A1 | 7/2011 | Redmond et al. | |
| 2012/0244604 A1* | 9/2012 | Kornilovich | B01L 3/50273 435/286.1 |
| 2013/0041236 A1 | 2/2013 | Pugia et al. | |
| 2013/0109030 A1* | 5/2013 | Hardeman | B01L 3/502715 435/7.1 |
| 2014/0170679 A1 | 6/2014 | Aitchison et al. | |
| 2014/0250985 A1 | 9/2014 | Shinobu et al. | |

FOREIGN PATENT DOCUMENTS

| | | |
|---|---|---|
| CN | 102985261 | 3/2013 |
| CN | 103249486 | 8/2013 |
| JP | 2013531222 | 8/2013 |
| JP | 2014173938 | 9/2014 |
| TW | 201248148 | 12/2012 |
| WO | WO-2006120656 A1 | 11/2006 |
| WO | WO-2007001912 | 1/2007 |
| WO | WO-2014178827 A1 | 11/2014 |
| WO | WO-2015006751 A1 | 1/2015 |
| WO | WO-2015116083 | 8/2015 |

OTHER PUBLICATIONS

Mcguinness; "Microfluidic Sensing Device"; Appln. No. PCT/US2014/137848; Filed Jan. 30, 2014.

* cited by examiner

VENTED MICROFLUIDIC RESERVOIRS

BACKGROUND

Microfluidics is a technology that applies across a variety of disciplines including engineering, physics, chemistry, microtechnology and biotechnology. Microfluidics involves the study of small volumes of fluid and how to manipulate, control and use such small volumes of fluid in various microfluidic systems and devices such as microfluidic chips. For example, microfluidic biochips (referred to as "lab-on-chip") are used in the field of molecular biology to integrate assay operations for purposes such as analyzing enzymes and DNA, detecting biochemical toxins and pathogens, diagnosing diseases, etc.

DETAILED DESCRIPTION

Microfluidic biochips can be employed in point of care testing to enable assay operations at a location associated with an individual to be tested. For example, in various point of care approaches to microfluidic testing a sample may be analyzed by a sensor in microfluidic testing device to give an indication of a disease state, among other possible conditions.

Some approaches to point of care testing employ sealed or open fluid collection basins. In either approach, the basins may serve to both collect a fluid sample to be analyzed and retain the fluid sample once analyzed and/or may rely on a microfluidic pump and/or gravity to convey an analyzed fluid sample (i.e., a volume of a fluid sample that has been tested) to the basins. Such approaches may not be suitably employed with a fluid sample communicated by an actuator (e.g., a thermal resistor) and a corresponding nozzle(s) into the basins as attempting to employ an actuator and/or a nozzle in such approaches may result in inaccuracies, such as those due to pressurizing the sealed fluid collection basin (e.g., pressurization at least in part to addition of air associated with the sample into the sealed fluid collection basin) and/or undesirably conveying some or all of the fluid sample (e.g., a pressurized fluid sample) to an environment surrounding the basin, among other difficulties.

Examples of the present disclosure include vented microfluidic reservoirs and methods, systems, and computer-readable media with executable instructions employed with the vented microfluidic reservoirs. Vented microfluidic reservoirs can, for example, include a housing and a vent coupled to the housing to vent air associated with a fluid sample (i.e., an analyzed fluid sample) communicated into the housing to an environment surrounding a microfluidic device coupled to the housing. In some examples, the vented microfluidic reservoirs may negate effects of air introduced with a fluid sample (e.g., introduced by actuation of an actuator via nozzle into the vented microfluidic reservoir) and store an analyzed fluid sample in the reservoir so it can be safely discarded (e.g., without leakage). Put another way, the vented microfluidic reservoirs can, for example, be employed with a nozzle in a microfluidic device that provides an ejection mechanism to move a fluid sample through the microfluidic device and into the vented microfluidic reservoirs. Notably, in such an example, the fluid sample is retained in the vented microfluidic reservoirs while air associated with the sample is vented, via a vent, to a surrounding environment in an effort to avoid pressurizing the reservoir while still retaining an entirety of the fluid sample in a volume of a housing of the vented microfluidic reservoirs.

Figure 1:
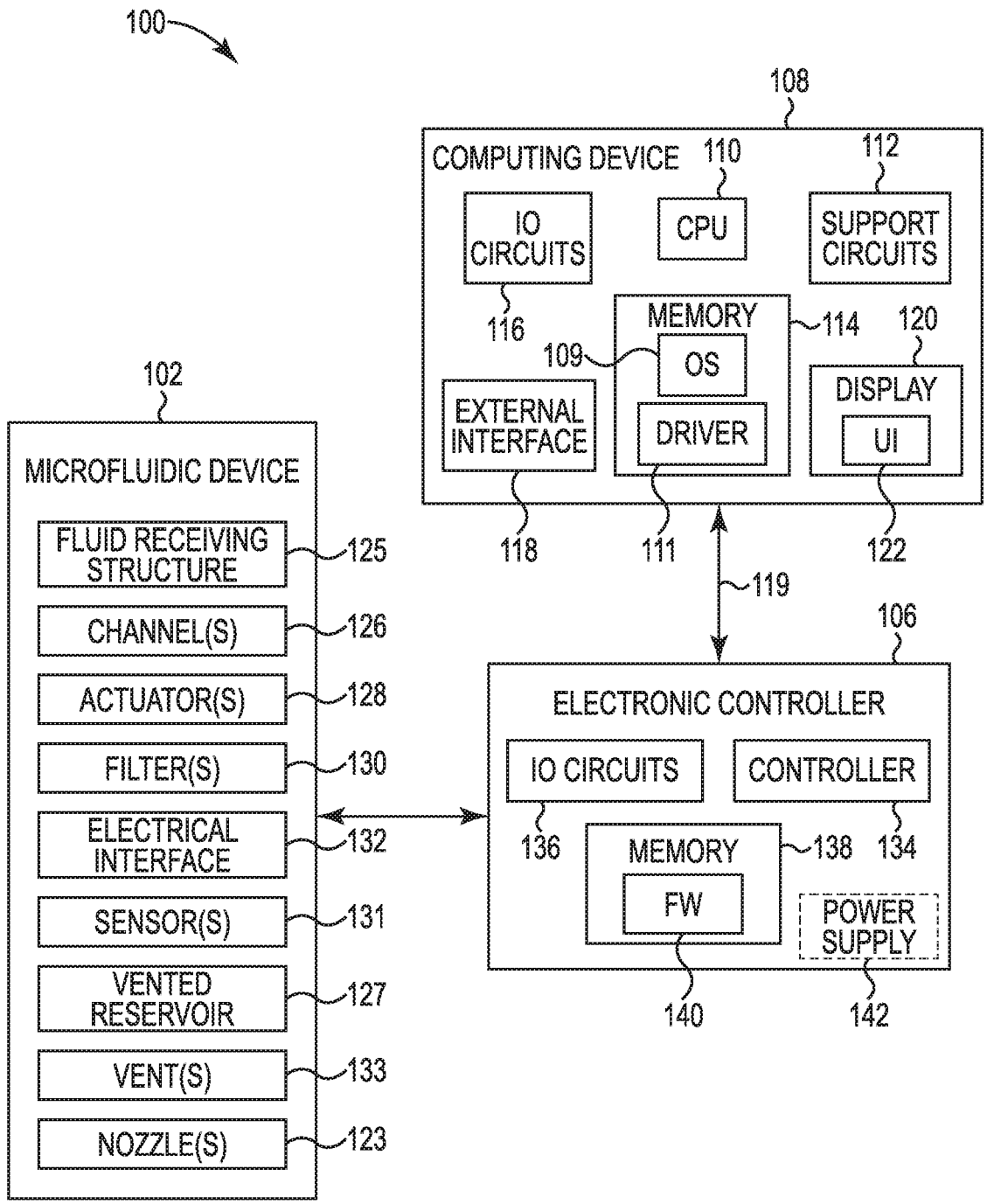
FIG. 1 illustrates a diagram of an example of a microfluidic diagnostic system including an example of a microfluidic device with a vented microfluidic reservoir according to the present disclosure.

FIG. 1 illustrates a diagram of an example of a microfluidic diagnostic system 100 including an example of a microfluidic device with a vented microfluidic reservoir according to the present disclosure. As illustrated in FIG. 1, the microfluidic diagnostic system 100 can include a microfluidic device 102, electronic controller 106, and/or the computing device 108. The microfluidic device 102 can include a fluid receiving structure 125, channel(s) 126, actuator(s) 128, filters(s) 130, an electrical interface 132, sensor(s) 131, a vented microfluidic reservoir (i.e., a vented reservoir), a vent(s) 133, and nozzle(s) 123. While the above described elements and configurations are illustrated in FIG. 1 the present disclosure is not so limited. Rather, more or less components can be included in the microfluidic diagnostic system 100, in the microfluidic device 102, and an electronic controller 106, and a computing device 108 and/or arranged in various configurations to promote vented microfluidic reservoirs, as described herein. Additionally while a particular number of elements are illustrated (e.g., a single channel 126) there can be more (e.g., two or more channels 126) and/or less of various elements such as the fluid receiving structure 125, the channel(s) 126, the actuator(s) 128, filters(s) 130, the electrical interface 132, the sensor(s) 131, the vented microfluidic reservoir, the vent(s) 133, and/or the nozzle(s) 123, etc. depending upon a desired application of the microfluidic diagnostic system 100.

In various examples, the microfluidic device 102 can be implemented as a chip-based device in some examples. For example, the structures and components of a chip-based microfluidic device 102 can be fabricated using integrated circuit microfabrication techniques such as electroforming, laser ablation, anisotropic etching, sputtering, dry and wet etching, photolithography, casting, molding, stamping, machining, spin coating, laminating, and so on.

The fluid receiving structure 125 refers to a structure having a volume to receive a fluid sample and communicate the same to the channel(s) 126 of the microfluidic device 102. That is, a fluid sample can be placed or otherwise provided to the fluid receiving structure 125. The fluid sample can be a fluid having particles (e.g., a blood sample, an ink containing particulate matter(s) such as a pigment(s), among other possible types of fluid). The fluid sample may pass through a filter(s) 130 disposed in the inlet(s) of the channel(s). The filter(s) 130 can prevent particles in the fluid sample of a particular size (depending on the size of the filter(s) 130 from entering the channel(s) 126.

The fluid receiving structure 125 can be located on and/or formed in an outer surface (i.e., a cassette) of the microfluidic device 102. However, the present disclosure is not so limited. The fluid receiving structure 125 can be coupled to and/or integral with an outer surface of the microfluidic device 102 and/or a microfluidic chip included in the microfluidic device. In various examples, a fluid sample can be introduced from the fluid receiving structure at an inlet(s) into the channels 126, passed through the channels(s) 126, processed by the microfluidic device 102, and communicated to a housing of the vented microfluidic reservoir 127 for storage therein.

In an example, the sensor(s) 131 is disposed in the channel(s) 126 near the inlet(s) (e.g., closer to the fluid receiving structure 125 than the actuator(s) 128). In another example, the sensor(s) 131 is disposed in the inlet of the channel(s) 126. The sensor(s) 131 can be an impedance sensor formed using various semiconductor formation techniques. The sensor(s) 131 can detect impedance changes as particles in the fluid sample pass over and/or near the sensor(s) 131.

The actuator(s) 128 is disposed near a closed end of the channel(s) 126 downstream from the sensors (131). The actuator(s) 128 can be implemented using a wide variety of structures suitable to communicate a fluid sample from the microfluidic device 102 to the vented reservoir 127. For example, the actuator(s) 128 can be a thermal resistor(s) that produces vapor bubbles to create fluid displacement of the fluid sample within the channel(s) 126. Actuators 128 can also be implemented as piezo elements (e.g., PZT) whose electrically induced deflections generate fluid displacements within the channel(s) 126. Other deflective membrane elements activated by electrical, magnetic, and other forces are also possible for use in implementing the actuator(s) 128. The displaced fluid sample can be ejected from the nozzle(s) 123 and/or moved within the channel(s) 126.

The nozzle(s) 123 refer to ejection nozzles suitable for use with actuator(s) 128. The nozzle(s) 123 disposed in or along the channel(s) 126. For example, nozzle(s) 123 can be adjacent to the sensor(s) 131 in the channel(s) 126.

The actuators 128 and/or the nozzle(s) 123 can directly or indirectly impart air along with the displaced fluid sample. Such air can be imparted into the channel(s) 126 and/or the vented microfluidic reservoir 127, among other components. In some other approaches to storing a fluid sample, imparting of air along with the fluid sample into a storage chamber may undesirably lead to pressurization of the storage chamber and/or undesirably impact a flow rate of the fluid sample into the storage chamber, among other undesired impacts of having air associated with a fluid sample. The vented microfluidic reservoir 127, as described herein, accounts for such air by allowing the air to be vented via a vent(s) 133, as described herein, coupled to a housing of the vented microfluidic reservoir to an environment surrounding the microfluidic device so the vented microfluidic reservoir 127 does not become pressurized (e.g., does not reach or maintain a pressurized state).

In some examples, the electronic controller 106 includes a controller 134, IO circuits 136, and a memory 138. The electronic controller 106 comprises a programmable device that includes machine-readable instructions, for example, on non-transitory processor and/or computer-readable media (e.g., the memory 138). It is to be understood that the electronic controller can execute instructions (illustrated as firmware 140), be implemented using hardware, instructions, or a combination thereof. For example, all or a portion of the electronic controller 106 can be implemented using a programmable logic device (PLD, application specific integrated circuit (ASIC), or the like. In some examples, the electronic controller 106 receives power from the computing device 108. The electronic controller 106 can include a power supply 142.

The electronic controller 106 is under control of the computing device 108. The computing device 108 can send and receive data to and from the electronic controller 106, including command information for controlling the microfluidic device 102 and sensor data obtained from the microfluidic device 102. The electronic controller 106 is coupled to the electrical interface 132 for energizing the actuator(s) 128 and sensor(s) 131. For instance, a fluid sample is passed by actuation via the actuator(s) 128 through channels 126, as described herein, and analyzed by a sensor(s) 131 included in the channels 126 under control of the electronic controller 106. The microfluidic device 102 provides an electrical output signal representing the sensor data to the electronic controller 106.

The computing device 108 includes a central processing unit (CPU) 110, various support circuits 112, memory 114, various input/output circuits 116, and an external interface 118. The CPU 110 can include any number of microprocessors capable of executing instructions stored by a memory 114. CPU 110 can be integrated in a single device or distributed across multiple devices (e.g., computing device and/or the microfluidic device, a server, etc.).

The memory 114 can include random access memory, read only memory, cache memory, magnetic read/write memory, or the like or any combination of such memory devices. Memory 114 can include a number of memory components capable of storing instructions that can be executed by CPU 110. Such memory 114 can be a non-transitory computer readable media. Memory 114 can be integrated in a single device or distributed across multiple devices. Further, memory 114 can be fully or partially integrated in the same device as CPU 110 or it can be separate but accessible to that device and CPU 110.

The memory 114 can store an operating system (OS) 109 and a driver 111. The OS 109 and the driver 111 can include instructions executable by the CPU 110 for controlling the computing device 108 and the electronic controller 106 through the external interface 118. The driver 111 provides a connection between the OS 109 and the electronic controller 106. Accordingly, the computing device 108 comprises a programmable device that includes machine-readable instructions, for example, on non-transitory processor/computer-readable media (e.g., the memory 114).

The support circuits 112 can include cache, power supplies, clock circuits, data registers, and the like. The circuits 116 can cooperate with the external interface 118 to facilitate communication with the electronic controller 106 over a communication medium 119. The external interface 118 can include a universal serial bus (USB) controller capable of sending and receiving data to the electronic controller 106, as well as providing power to the electronic controller 106, over a USB cable. It is to be understood that other types of electrical, optical, or RF interfaces to the electronic controller 106 can be used to send and receive data and/or provide power. The communication medium 119 can be any type of electrical, optical, radio frequency (RF), or the like transfer path.

The computing device 108 can include a display 120 through which the OS 109 can provide a user interface (UI) 122. A user can use the UI 122 to interact with the OS 109 and the driver 111 to control the electronic controller 106, and display data received from the electronic controller 106. As used herein, a user can refer to a healthcare professional and/or an individual to be tested (i.e., a patient). However, examples are not so limited, and a user can refer to any type of user other than healthcare professionals and/or a user to be tested. The computing device 108 can also display data received from the electronic controller 106 and/or the microfluidic device 102. In some examples, the computing device 108 can be a device such as a "smart phone", a tablet computer, or other types of suitable computing devices to promote vented microfluidic reservoirs, as described herein.

Figure 2:
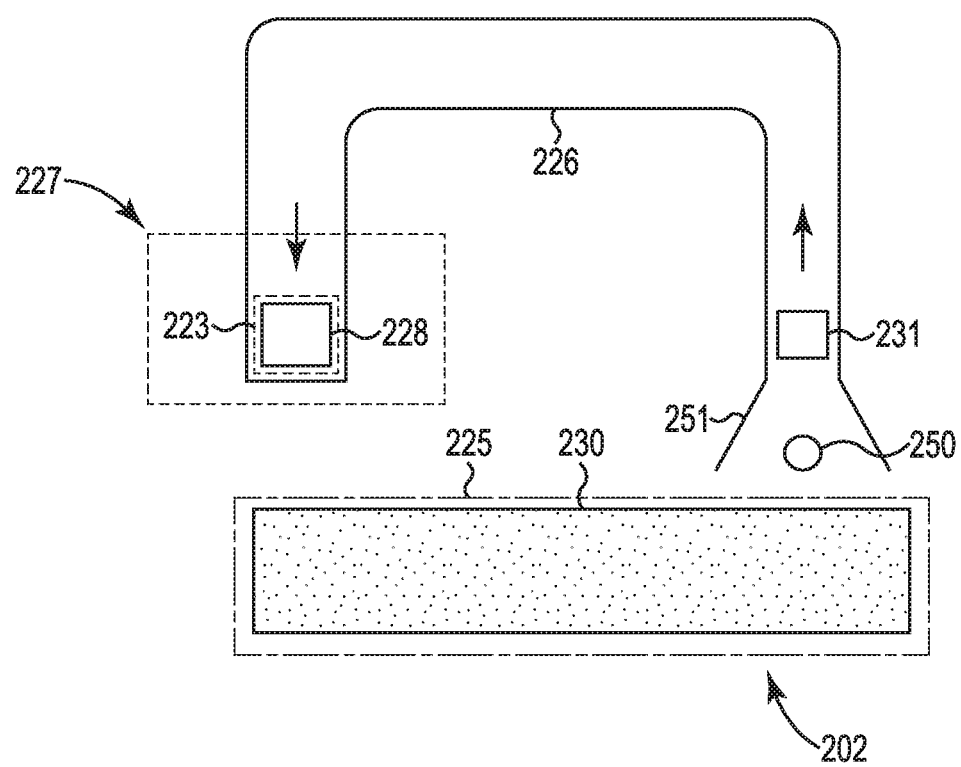
FIG. 2 illustrates a schematic diagram of an example of a microfluidic device including a vented microfluidic reservoir according to the present disclosure.

FIG. 2 illustrates a schematic diagram of an example of a microfluidic device including a vented microfluidic reservoir 202 according to the present disclosure. The microfluidic device 202 includes a channel 226 (i.e., a microfluidic channel), an actuator 228, a sensor 231, an inlet 251 to receive a fluid sample 250 from a fluid receiving structure 225, and a nozzle(s) 223 (e.g., an outlet from the channel 226 to a vented microfluidic reservoir 227). In an example, a filter 230 (e.g., a mesh filter) can be provided in the fluid receiving device 225 for filtering particles in the applied fluid sample. While the shape of the fluid channel 226 is shown as being "u-shaped", this is not intended as a limitation on the shape of the channel 226. Thus, the shape of the channel 226 can include other shapes, such as curved shapes, snake-like shapes, shapes with corners, combinations thereof, and so on. Moreover, the channel 226 is not shown to any particular scale or proportion. The width of the channel 226 as fabricated on a device can vary from any scale or proportion shown in the drawings of this disclosure. The arrows in the channel indicate an example of a direction of fluid flow of a fluid sample through the channel 226.

The inlet 251 provides an opening for the channel 226 to receive the fluid sample. The filter 230 is disposed in the inlet 251. The filter 230 prevents particles in the fluid sample of a particular size (depending on the size of the filter 230) from entering the channel 226. The inlet 251 can have a larger width and volume than the channel 226. That is, a volume of the inlet 251 can be greater than a volume of the channel 226. Inlet can enable a fluid sample to flow from the fluid receiving structure 225 into the channel 226.

In some examples, the sensor 231 is disposed in the channel 226. The sensor 231 can be an impedance sensor formed using various semiconductor techniques. The sensor 231 can detect impedance changes as particles in the fluid sample pass over the sensor 231.

The actuator 228 is disposed near a closed end of the channel 226 downstream from the sensor 231. The actuator 228 can be a fluidic inertial actuator, which can be implemented using a wide variety of structures. For example, the actuator 228 can be a thermal resistor that produces vapor bubbles to create fluid displacement within the channel 226. The displaced fluid sample can be ejected from the nozzle(s) 223 into a vented fluid reservoir 227.

Figure 3:
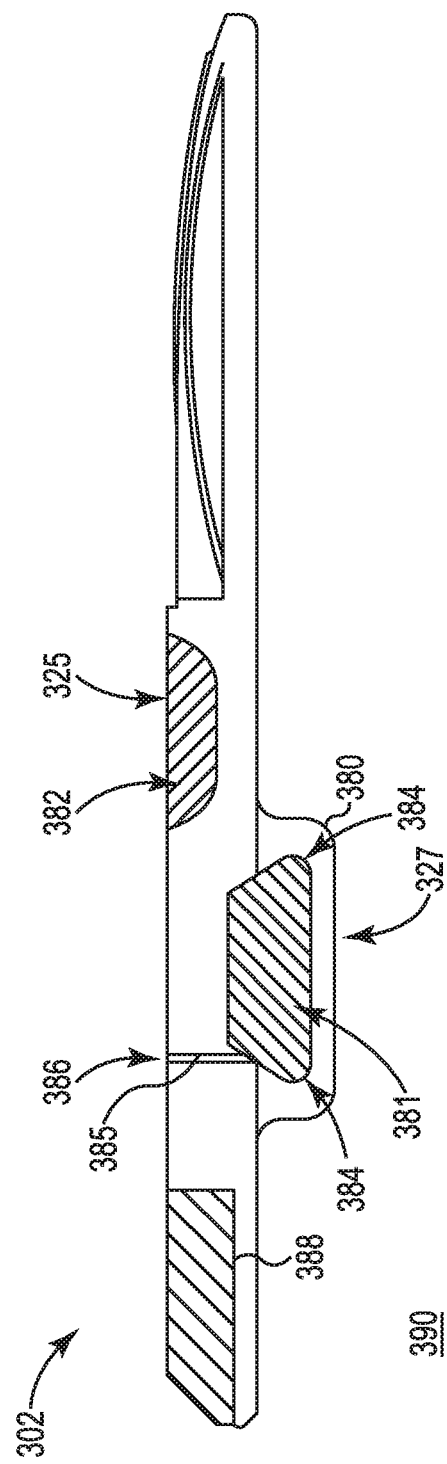
FIG. 3 illustrates a diagram of a side view of an example of a microfluidic device including a vented microfluidic reservoir according to the present disclosure.

FIG. 3 illustrates a diagram of a side view of an example of a microfluidic device including a vented microfluidic reservoir according to the present disclosure. The microfluidic device 302 includes a housing 380 coupled to the microfluidic device 302 to provide fluid communication of a fluid sample from a fluid receiving structure 325 of the microfluidic device 302 through a channel (not shown in FIG. 3 for ease of illustration) of the microfluidic device 302 by a sensor (not shown) in the channel into the housing 380 and can include a vent 386 coupled to the housing 380 (e.g., coupled by a vent tube 385) to vent air associated with the fluid sample communicated into the housing 380 to an environment 390 surrounding the microfluidic device 302.

While other configurations and/or orientations are possible, in some examples, the microfluidic device 302 includes a fluid receiving structure 325, as described herein, located on a top portion of the vented microfluidic reservoir 327 and the vented microfluidic reservoir 327 located on a bottom portion of the vented microfluidic fluid) introduced into the fluid receiving structure 325 can pass through a fluidic path including vented reservoir 327, as illustrated in FIG. 3. Put another way, in some examples, the vented microfluidic reservoir 327 including a housing thereof is located on an opposing side of a microfluidic device chip and/or the microfluidic device relative to the fluid receiving structure. The fluid receiving structure 325 and the vented microfluidic reservoir 327 are in fluid communication such that a fluid sample (e.g., at least a portion of the sample channel(s), actuators(s), nozzle(s), among other component described herein that have been omitted in FIG. 3 for ease of illustration, into the vented microfluidic reservoir 327.

The vented microfluidic reservoir 327 can, in various examples, include a housing 380 or other structure substantially enclosing and defining a volume 381 of the vented microfluidic reservoir 327. For example, the housing 380 can enclose the volume 381 other than at opening(s) in the housing 380 permitting communication of a fluid sample into the housing and/or permitting air associated with a fluid sample to be vented from the vented microfluidic reservoir 327 via the vent 386). It is noted that the fluid receiving structure 325 has a volume 382 that is less than a volume of the vented microfluidic reservoir 325. For instance, in some examples, the volume of the vented microfluidic reservoir is in a range from 15 picoliters to 1000 microliters. All individual values and subranges from 15 picoliters to 1000 microliters are included; for example, the volume of the vented microfluidic reservoir can have from a lower limit of 15 picoliters, 50 picoliters, or 75 picoliters to an upper limit of 1000 microliters, 500 microliters, or 1 microliters of the total weight of the polyether-acetal polyol. A volume of a vent tube, as described herein, is not included in the volume of the vented microfluidic reservoir.

The housing 380 and/or a vent tube 386, as describe herein, can be made of a same or different material as the microfluidic device 302. The housing 380 can be coupled to and/or integral with an outer surface the microfluidic device 302. For instance, in some examples, the housing 380 is integral with the microfluidic device and not removable therefrom. Such examples can promote safe storage of a fluid sample (e.g., without spilling) in applications such as those involving bio fluids or otherwise sensitive fluids and/or in single use applications, among other applications.

Notably, the volume 381 can include a grooved region 384 or regions that can act as wetting surface(s) (e.g., enable substantially uniform flow of a fluid sample into and/or throughout the vented microfluidic reservoir 327) to promote communication of fluid to and/or storage of fluid in the grooved region 384. That is, housing 381 can include a grooved region 384 located along at least a portion of a periphery of the housing 381 (e.g., located continuously along a periphery of the housing 381) to retain at least some of the fluid sample in the grooved region. While illustrated for ease of illustration in FIG. 3 as substantially flat and level with a lower portion of the volume 381 of the housing 380, the grooved region can be varied in size and/or shape to retain some or all of a fluid sample communicated to the vented microfluidic reservoir 327 depending upon a desired application. For example, the grooved region 384 can be a "U-shaped" region extending partially into housing 380 suitable to retain a fluid sample therein, among other possible shapes. In some examples, grooved region 384 can extend into another portion of the lower portion of the volume 381 other than along the periphery of the housing.

Systems employing vented microfluidic reservoirs can, in various examples, include a vented microfluidic reservoir including a housing defining a volume of the vented microfluidic reservoir, an ejection nozzle(s) to cause flow of a fluid sample into the volume of the vented microfluidic reservoir; and a vent coupled to the vented microfluidic reservoir to vent air imparted by the flow of the fluid sample into the housing, among other components such as those described herein. In some examples, the systems can include a housing having a grooved region, as described herein, located along a periphery of the housing to retain at least some of a fluid sample in the grooved region. As illustrated in FIG. 3, systems can have the vented microfluidic reservoir located on a bottom of a microfluidic device relative to an electrical interface located on a side of the microfluidic device. In some examples, the vent can be located proximate to an interface with a computing device of the microfluidic device.

A vent tube 385 couples the vent 386 to the vented microfluidic reservoir 327. Vent tube 385 refers to a conduit formed at least partially in (e.g., passing through at least a portion of) the microfluidic reservoir. The vent tube 385 can be formed at least partially within the microfluidic device 302 reservoir, for instance, through a machining and/or a lamination process(es), among other suitable processes to form the vent tube 385. In some examples, the vent tube 385 is formed entirely within the microfluidic device 302 (i.e., internally within) in a manner to convey air from the microfluidic reservoir 327 to vent 386 without any openings other than at the respective ends of the vent tube 385 (e.g., an opening at the vent 386 and an opening in a housing of the vented microfluidic reservoir 327). That is, the vent tube 385 provides an indirect path for air imparted by the flow of at least a subset of the fluid sample into a housing 380 of the vented microfluidic reservoir 327 to exit therefrom. The vent 386 is a fixed, unobstructed orifice.

For example the vent tube can be coupled to an opening in the housing 380 of the vented microfluidic reservoir 327 that is different than (e.g., separate and distinct from an opening associated with an inlet from a channel(s) into the microfluidic reservoir 327. Vent tube 385 is separate and distinct from the channel(s) providing a fluid sample and air associated with the fluid sample to the vented microfluidic reservoir 380. That is, the fluid sample is provided to the vented microfluidic reservoir 380 by the channel(s) that is a different structure than a structure of the vent tube 385. For example, the vent tube can be a dedicated vent tube that is not coupled to a fluid receiving structure. Similarly, the vent 386 is separate and distinct from the fluid receiving structure 325. In some examples, the vent 386 can be located proximate to (e.g., included in or near) an electrical interface 388. In some examples, the electrical interface can be proximate with a computing device (e.g., when the microfluidic device is coupled to the computing device) and/or a portion of a chip on a chip based microfluidic device 302. Electrical interface 388 can provide a coupling point between a computing device and the microfluidic device 302 and/or provided a point of attachment suitable to attach at least a portion of a chip, enable communication (e.g., communication of commands from the computing device to the microfluidic device to operate elements such as the actuators, sensors, etc. of the microfluidic device), among other possibilities. Positioning the vent 386 proximate the electrical interface 388 can ensure adequate separation between electronics that may be included in the electrical interface 388 and a fluid sample placed into the microfluidic device 302 via the fluid receiving structure 325.

While FIG. 3 illustrates a single vent tube 385 and single vent 386, the present disclosure is not s so limited. That is, vent tube 385 can be included in a plurality of vent tubes 385 each in communication (e.g., fluid communication) with a vent(s) and/or a single vent tube 385 can be in communication with a plurality of vents, among other possibilities.

In some examples, vent tube 385 can be formed of the same material as the microfluidic device (e.g., a material forming the outer surface (i.e., a cassette) of the microfluidic device 302). However, the present disclosure is not so limited. That is vent tube can be formed entirely or in part of a different material than the microfluidic device. Examples of suitable materials to form the vent tube 385 include silicon, epoxy, plastic, metal, and/or combinations thereof, among other materials suitable to form the vent tube 385.

Figure 4:
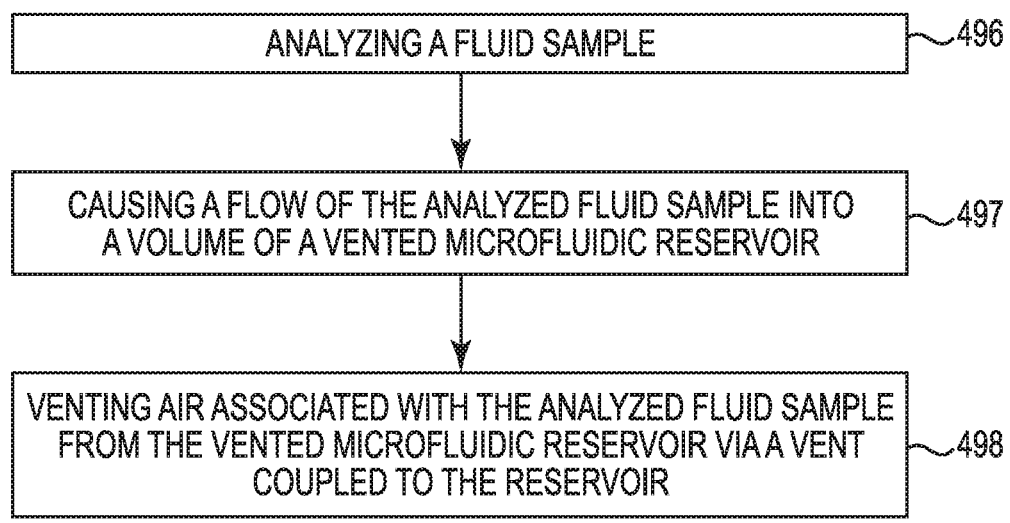
FIG. 4 illustrates a flow diagram of an example of a method employing a vented microfluidic reservoir according to the present disclosure.

FIG. 4 illustrates a flow diagram of an example of a method employing a vented microfluidic reservoir according to the present disclosure. As shown at 496, in various examples, the method can include analyzing a fluid sample. Analyzing can include utilizing a sensor such as those describe herein to measure various information and/or properties (e.g., impedance) of a sample.

The method can include causing a flow of the analyzed fluid sample into a volume of a vented microfluidic reservoir, as shown at 497. Causing refers to causing a flow of the sample, for instance, by actuation of actuators and/or nozzles, as described herein. Such a flow egress from the nozzles into the vented microfluidic reservoir. That is, causing a flow of the analyzed fluid sample ensures introducing a flow of at least the subset of the analyzed fluid sample from the channel(s) into the vented microfluidic reservoir.

In some examples, the method can include introducing a volume of an analyzed fluid sample into the vented microfluidic reservoir where the vented microfluidic reservoir has a greater volume than a volume of a fluid receiving structure. Put another way, in such examples, the volume of the analyzed fluid caused to flow into the vented microfluidic reservoir is less than a volume of the vented microfluidic reservoir. That is, the comparatively large volume of the vented microfluidic reservoir relative to the fluid receiving structure promotes retaining all of a fluid sample (e.g., all of an analyzed fluid sample) in the vented microfluidic reservoir.

As shown at 498, the method can include venting air associated with (included in the fluid sample and/or entering the vented microfluidic reservoir along with the fluid sample) the analyzed fluid sample from the vented microfluidic reservoir via a vent coupled to the reservoir, as described herein.

In the foregoing detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and that process, electrical, and/or structural changes may be made without departing from the scope of the present disclosure.

The figures herein follow a numbering convention in which the first digit corresponds to the drawing figure number and the remaining digits identify an element or component in the drawing. For example, reference numeral 100 may refer to element "00" in FIG. 1 and an analogous element may be identified by reference numeral 200 in FIG. 2. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure, and should not be taken in a limiting sense. Further, as used herein, "a number of" an element and/or feature can refer to an element(s) and/or feature(s).

As used herein, "logic" is an alternative or additional processing resource to perform a particular action and/or function, etc., described herein, which includes hardware, e.g., various forms of transistor logic, application specific integrated circuits (ASICs), etc., as opposed to computer executable instructions, e.g., software firmware, etc., stored in memory and executable by a processor.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present.

As used herein, the term "and/or" includes any and all combinations of a number of the associated listed items. As used herein the term "or," unless otherwise noted, means logically inclusive or. That is, "A or B" can include (only A), (only B), or (both A and B). In other words, "A or B" can mean "A and/or B" or "one or more of A and B."

What is claimed:

1. A microfluidic device, comprising:
   a microfluidic chip comprising:
      a fluid receiving structure,
      a channel,
      a sensor in an inlet of the channel, and
      a nozzle and actuator in the channel to create fluid displacement and direct a fluid sample into a vented microfluidic reservoir; and
   the vented microfluidic reservoir including:
      a housing, separate from the microfluidic chip, that is coupled to the microfluidic chip to enclose a volume below the microfluidic chip that is in communication with the channel through the nozzle to provide fluid communication of the fluid sample from the fluid receiving structure through the channel by the sensor via the nozzle into the housing, wherein the volume is partially defined in the microfluidic chip and is enclosed for fluid flow with a single opening for communication of the fluid sample into the housing; and
      a vent tube coupled to the volume enclosed by the housing; and
      a vent coupled to the vent tube to vent air associated with the fluid sample communicated into the housing to an environment surrounding the microfluidic device.

2. The microfluidic device of claim 1, where the vent tube is separate and distinct from the channel.

3. The microfluidic device of claim 1, where the housing is located on a bottom side of the microfluidic chip and the fluid receiving structure is located on a top side of the microfluidic chip.

4. The microfluidic device of claim 1, where the housing comprises a grooved portion arranged continuously around a periphery of the reservoir to draw the fluid sample toward the periphery of the reservoir.

5. The microfluidic device of claim 1, where an actuator is located downstream from the sensor.

6. The microfluidic device of claim 1, where the vent is located on an exterior surface of the microfluidic device at a location other than an exterior surface of the housing of the reservoir.

7. The microfluidic device of claim 1, wherein the housing and vent tube are of a different material as the remainder of the microfluidic device.

8. The microfluidic device of claim 1, further comprising a filter.

9. The microfluidic device of claim 8, wherein the filter is formed in an inlet of the fluid receiving structure.

10. The microfluidic device of claim 1, wherein the channel is a u-shaped channel.

11. The microfluidic device of claim 1, wherein the sensor is an impedance sensor.

12. The microfluidic device of claim 1, wherein the vent tube is formed of silicon.

13. The microfluidic device of claim 1, wherein the vent tube is formed of metal.

14. The microfluidic device of claim 1, wherein:
   the vented microfluidic reservoir is disposed adjacent to the fluid receiving structure; and
   the fluid receiving structure is located above the vented microfluidic structure.

15. A microfluidic device, comprising:
   a microfluidic chip; and
   a vented microfluidic reservoir coupled to the microfluidic chip;
   the microfluidic chip further comprising:
      a fluid receiving structure to receive a fluid sample,
      a channel fluidly communicating between the fluid receiving structure and the vented microfluidic reservoir,
      an electronic sensor in the channel between the fluid receiving structure and the vented microfluidic reservoir to test a fluid sample moving from the fluid receiving structure to the microfluidic reservoir, and
      an actuator associated with an ejection nozzle to cause flow of the fluid sample through the channel, over the sensor and into the vented microfluidic reservoir, wherein the electronic sensor is closer to the fluid receiving structure than the actuator; and
   the vented microfluidic reservoir further comprising:
      a housing of the reservoir, the housing being coupled to the microfluidic chip to enclose a volume below that microfluidic chip that is in communication with the channel through the ejection nozzle to provide fluid communication of a fluid sample from the fluid receiving structure through the channel by the electronic sensor via the ejection nozzle into the housing, wherein the volume is partially defined in the microfluidic chip,
      a vent tube providing a passageway for air out of the reservoir,
      a vent coupled to the vent tube to vent air from the reservoir to an environment surrounding the microfluidic device, and
      a grooved portion around a periphery of the reservoir to draw the fluid sample toward the periphery of the reservoir.

16. The microfluidic device of claim 15, where the fluid receiving structure has a volume that is less than a volume of the vented microfluidic reservoir.

17. The microfluidic device of claim 15, wherein the actuator is located downstream from the sensor.

18. A system, comprising:
- a microfluidic chip comprising a fluid receiving structure, a channel, and a sensor in an inlet of the channel;
- a vented microfluidic reservoir including a housing to enclose a volume of the vented microfluidic reservoir below the microfluidic chip, which volume is in communication with the channel through a nozzle to provide fluid communication of a fluid sample from the fluid receiving structure through the channel by the sensor via the nozzle into the housing, wherein:
  - the volume is partially defined in the microfluidic chip; and
  - the housing comprises a U-shaped groove region located along a periphery of the housing to retain fluid in the grooved region;
- an actuator associated with an ejection nozzle to cause flow of a fluid sample into the volume of the vented microfluidic reservoir, wherein the sensor is closer to the fluid receiving structure than the actuator; and
- a vent tube coupled to the vented microfluidic reservoir and multiple vents to vent air associated with flow of the fluid sample into the housing.

19. The system of claim 18, where the actuator imparts air along with fluid sample.

20. The system of claim 18, where the vent is located proximate to an electrical interface comprising a Universal Serial Bus for connecting the system to an electronic controller.

* * * * *